(12) United States Patent
Noll et al.

(10) Patent No.: US 11,052,037 B2
(45) Date of Patent: Jul. 6, 2021

(54) STYLING CREAM FOR THE TEMPORARY SHAPING OF HAIR

(71) Applicant: Henkel AG & Co. KGaA, Duesseldorf (DE)

(72) Inventors: Marcus Noll, Quickborn (DE); Anna Puls, Winsen (DE); Sandra Brandt, Pinneberg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/694,461

(22) Filed: Nov. 25, 2019

(65) Prior Publication Data

US 2020/0179265 A1 Jun. 11, 2020

(30) Foreign Application Priority Data

Dec. 11, 2018 (DE) ...................... 10 2018 221 404.2

(51) Int. Cl.
| | |
|---|---|
| *A61K 8/92* | (2006.01) |
| *A61K 8/25* | (2006.01) |
| *A61K 8/34* | (2006.01) |
| *A61K 8/81* | (2006.01) |
| *A61K 8/891* | (2006.01) |
| *A61Q 5/06* | (2006.01) |

(52) U.S. Cl.
CPC ................ *A61K 8/927* (2013.01); *A61K 8/25* (2013.01); *A61K 8/342* (2013.01); *A61K 8/8135* (2013.01); *A61K 8/8182* (2013.01); *A61K 8/891* (2013.01); *A61Q 5/06* (2013.01); *A61K 2800/59* (2013.01); *A61K 2800/621* (2013.01)

(58) Field of Classification Search
CPC ........................................................ A61Q 5/06
See application file for complete search history.

(56) References Cited

U.S. PATENT DOCUMENTS

| | | | |
|---|---|---|---|
| 2005/0265943 A1* | 12/2005 | Geffroy-Hyland | A61Q 1/00 424/70.12 |
| 2010/0209376 A1* | 8/2010 | Richters | A61K 8/375 424/70.12 |
| 2018/0243204 A1* | 8/2018 | Parikh | A61K 8/342 |

FOREIGN PATENT DOCUMENTS

| | | |
|---|---|---|
| EP | 2266532 A2 | 12/2010 |
| GB | 2423250 A | 8/2006 |
| WO | 2009056398 A2 | 5/2009 |

* cited by examiner

*Primary Examiner* — Bethany P Barham
*Assistant Examiner* — Barbara S Frazier
(74) *Attorney, Agent, or Firm* — Lorenz & Kopf, LLP

(57) ABSTRACT

A cosmetic composition for temporarily shaping hair includes, in a cosmetically acceptable support—respectively with respect to the total weight of the composition—
  e) from about 0.5% to about 8% by weight of a wax with a melting point of more than about 37° C.,
  f) from about 0.5% to about 5% by weight of a fatty alcohol,
  g) from about 0.2% to about 2% by weight of a vinylpyrrolidone-containing polymer or copolymer, and
  h) from about 0.1% to about 10% by weight of composite powder comprising
  (A) powdered particles of a silicone elastomer, and
  (B) particles of silicon dioxide,
  wherein the particles of silicon dioxide (B) are immobilized on the surface of the powdered particles of the silicone elastomer (A).

8 Claims, No Drawings

US 11,052,037 B2

STYLING CREAM FOR THE TEMPORARY SHAPING OF HAIR

CROSS-REFERENCE TO RELATED APPLICATION

This application claims priority to German Patent Application No. 10 2018 221 404.2, filed Dec. 11, 2018, which is incorporated herein by reference in its entirety.

TECHNICAL FIELD

The present disclosure describes a cosmetic composition for the temporary shaping of hair, which comprises water, wax and a fatty alcohol, as well as the use thereof. In addition, a method for the temporary shaping of hair using the cosmetic composition is disclosed.

BACKGROUND

Cosmetic compositions which serve to permanently or temporarily shape the hair (styling) play an important role in cosmetics. Thus, many cosmetic compositions are known in the prior art, such as, for example, hair sprays, hair waxes, hair gels, hair foams, pomades, styling powders, styling clays, hair lotions, etc.

These styling products not only differ in how they are applied to the hair (by spraying, by applying with the hand, by applying using a comb, etc.), but in particular in their consistency and their purpose (styling result). Thus, hair sprays in particular serve to make an already styled hairstyle hold for a longer period. Pomades were initially developed in order to make the hair smooth and neat and at the same time to obtain a very glossy finish. Styling creams (also known as hair lotions)—these have a consistency that resembles a lotion (in contrast to the solid pasty consistency of pomades and pastes) and in particular can control and condition curly/frizzy hair because of their moisturizing properties. Styling creams offer an easy, softer hold compared with all other hair styling products.

As a rule, the styling products mentioned above include firming substances and in fact usually include synthetic polymers and/or waxes. The hold of the hairstyle is essentially determined by the type and quantity of the firming substances employed.

Many consumers want a styling result that looks natural, where the hair does not feel sticky or hard, but rather feels smooth and groomed.

In order to obtain a natural styling result with the desired hold (for example light or medium), a combination of synthetic polymers and waxes is regularly employed. However, it has been observed that when using vinylpyrrolidone-containing polymers or copolymers as the firming substances, the waxes and optional other components of the styling agents which are used plasticize them, with the result that the styling product as a whole becomes sticky.

There is also a need for styling products including a vinylpyrrolidone-containing polymer and/or copolymer as well as a wax which provides the hair treated with it with a high hold and also which endows the hair treated with it with a groomed and non-sticky hair feel.

BRIEF SUMMARY

This disclosure provides a cosmetic composition for temporarily shaping hair includes, in a cosmetically acceptable support—respectively with respect to the total weight of the composition— a) from about 0.5% to about 8% by weight of a wax with a melting point of more than about 37° C.,
b) from about 0.5% to about 5% by weight of a fatty alcohol,
c) from about 0.2% to about 2% by weight of a vinylpyrrolidone-containing polymer or copolymer, and
d) from about 0.1% to about 10% by weight of composite powder comprising
  (A) powdered particles of a silicone elastomer, and
  (B) particles of silicon dioxide,
  wherein the particles of silicon dioxide (B) are immobilized on the surface of the powdered particles of the silicone elastomer (A).

This disclosure also provides a method for temporarily shaping hair in which the cosmetic composition is applied to the hair and the hair is temporarily fixed into shape.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

This objective is achieved by employing a cosmetic composition for temporarily shaping hair comprising, in a cosmetically acceptable support—respectively with respect to the total weight of the composition— a) from about 0.5% to about 8% by weight of a wax with a melting point of more than 37° C.,
b) from about 0.5% to about 5% by weight of a fatty alcohol,
c) from about 0.2% to about 2% by weight of a vinylpyrrolidone-containing polymer or copolymer, and
d) from about 0.1% to about 10% by weight of composite powder consisting of or including
  (A) powdered particles of a silicone elastomer, and
  (B) particles of silicon dioxide, wherein the particles of silicon dioxide (B) are immobilized on the surface of the powdered particles of the silicone elastomer (A).

Surprisingly, it has been established that, despite the simultaneous presence of a vinylpyrrolidone-containing (co)polymer and a wax or copolymer, hair treated with a cosmetic composition of this type for temporarily shaping hair delivers a high hold without making the hair sticky. Furthermore, a composition of this type can be distributed very well and evenly in the hair.

As the first essential ingredient, the cosmetic composition for the temporary shaping of hair includes a) at least one natural or synthetic wax which has a melting point of more than about 37° C. The cosmetic agent includes the at least one wax in a total quantity of from about 0.5% to about 8% by weight, preferably from about 1% to about 6% by weight and yet more preferably from about 1.5% to about 5% by weight, with respect to the total weight of the cosmetic composition.

Solid paraffins or isoparaffins, vegetable waxes such as candelila wax, carnauba wax, esparto grass wax, Japan wax, cork wax, cane sugar wax, ouricury wax, montan wax, sunflower wax, fruit waxes and animal waxes such as, for example, beeswax and other insect waxes, sperm whale oil, shellac wax, lanolin and rump fat, also mineral waxes such as, for example, ceresin and ozokerite or petrochemical waxes such as, for example, petroleum jelly, paraffin waxes, microwaxes from polyethylene or polypropylene and polyethylene glycol waxes may be used as the natural or synthetic waxes. It may be advantageous to use hydrogenated or hardened waxes. Furthermore, chemically modified waxes may also be used, in particular hard waxes, for example montan ester waxes, Sasol waxes and hydrogenated jojoba waxes.

Triglycerides of saturated and optionally hydroxylated C16-30 fatty acids such as, for example, hardened triglyceride fats (hydrogenated palm oil, hydrogenated coconut oil, hydrogenated castor oil, glyceryl tribehenate or glyceryl tri-12-hydroxystearate, also synthetic full esters formed from fatty acids and glycols (for example Syncrowachs®) or polyols containing 2-6 C atoms, fatty acid monoalkanolamides containing a C12-22 acyl residue and a C2-4 alkanol residue, esters formed from saturated and/or unsaturated, branched and/or unbranched alkanecarboxylic acids with a chain length of 1 to 80 C atoms and saturated and/or unsaturated, branched and/or unbranched alcohols with a chain length of 1 to 80 C atoms including, for example, synthetic fatty acid fatty alcohol esters such as stearyl stearate or cetyl palmitate, esters formed from aromatic carboxylic acids, dicarboxylic acids or hydroxycarboxylic acids (for example 12-hydroxystearic acid) and saturated and/or unsaturated, branched and/or unbranched alcohols with a chain length of 1 to about 80 C atoms, lactides of long chain hydroxycarboxylic acids and full esters formed from fatty alcohols and dicarboxylic acids and tricarboxylic acids, for example, for example dicetyl succinate or dicetyl-/stearyl adipate, as well as mixtures of these substances, are also suitable.

The wax components may also be selected from the group formed by esters of saturated, unbranched alkanecarboxylic acids with a chain length of about 14 to about 44 C atoms and saturated, unbranched alcohols with a chain length of about 14 to about 44 C atoms, as long as the wax components or the totality of the wax components are solid at room temperature. The wax components may, for example, be selected from the group formed by C16-36 alkyl stearates, C10-40 alkyl stearates, C2-40-alkyl isostearates, C20-40 dialkyl esters of dimeric acids, C18-38 alkylhydroxystearoyl stearates, C20-40 alkyl erucates, and furthermore, C30-50-alkyl beeswax as well as cetearyl behenate may be used. In addition, silicone waxes, for example stearyl trimethylsilane/stearyl alcohol, may also be advantageous. Preferred wax components are the esters of saturated, monovalent C20-C60 alcohols and saturated C8-C30 monocarboxylic acids, in particular a C20-C40 alkyl stearate which can be obtained from Koster Keunen Inc. under the name Kesterwachs® K82H.

Natural, chemically modified and synthetic waxes may be used alone or in combinations. The teaching of the present disclosure thus also encompasses the combined use of a plurality of waxes. Furthermore, a series of wax mixtures, optionally mixed with other additives, are commercially available. Examples of mixtures which could be used are those with the names "Spezialwachs 7686 OE" (a mixture of cetyl palmitate, beeswax, microcrystalline wax and polyethylene with a melting range of from about 73 to about 75° C.; manufacturer: Kahl & Co), Polywax® GP 200 (a mixture of stearyl alcohol and polyethylene glycol stearate with a melting point of from about 47 to about 51° C.; manufacturer: Croda) and "Weichceresin® FL 400" (a Vaseline/Vaseline oil/wax mixture with a melting point of from about 50 to about 54° C.; manufacturer: Parafluid Mineralölgesellschaft).

Preferably, the wax a) is a natural wax. Extremely preferably, the natural wax comprises or is beeswax (INCI: Beeswax Cera Alba).

The wax provides the cosmetic composition with its consistency. In addition, the wax endows the hair that has been treated with it with feel and thus provides it with control.

The cosmetic composition includes a fatty alcohol as the second essential ingredient.

A "fatty alcohol" is any fatty alcohol with a carbon chain of C5 or more. As an example, the fatty alcohol may be selected from $C_9$-$C_{11}$ fatty alcohols, $C_{12}$-$C_{13}$ fatty alcohols, $C_{12}$-$C_{15}$ fatty alcohols, $C_{12}$-$C_{16}$ fatty alcohols, $C_{14}$-$C_{15}$ fatty alcohols, arachidyl alcohol, behenyl alcohol, capryl alcohol, cetearyl alcohol, cetyl alcohol, coco salcohol, decyl alcohol, (hydrogenated) tallow alcohol, lauryl alcohol, myristyl alcohol, oleyl alcohol, palm alcohol, palm kernel alcohol, stearyl alcohol and/or tridecyl alcohol.

in a particularly preferred embodiment of the cosmetic composition, the fatty alcohol comprises cetearyl alcohol. In a more particularly preferred embodiment of the cosmetic composition, the fatty alcohol is cetearyl alcohol.

The quantity of the fatty alcohol is from about 0.5% to about 5% by weight, preferably from about 0.75% to about 4% by weight and particularly preferably from about 1% to about 2.5% by weight, respectively with respect to the total quantity of the cosmetic composition.

The cosmetic composition includes a vinylpyrrolidone-containing polymer or copolymer as the third essential ingredient.

Particularly preferably, the vinylpyrrolidone-containing polymer or copolymer is selected from the group including polyvinylpyrrolidone, vinylpyrrolidone-vinyl acetate copolymer, vinyl caprolactam/VP/Dimethylaminoethyl Methacrylate Copolymer (INCI), VP/DMAPA Acrylates Copolymer (INCI) and mixtures thereof.

By way of example, suitable polyvinylpyrrolidones may be obtained from BASF SE under the trade description Luviskol® K. More particularly preferred vinylpyrrolidone-containing copolymers which are employed in the cosmetic compositions are a styrene/VP copolymer and/or a vinylpyrrolidone-vinyl acetate copolymer and/or a VP/DMAPA Acrylates Copolymer and/or a VP/vinyl caprolactam/DMAPA Acrylates Copolymer.

Vinylpyrrolidone-vinyl acetate copolymers are marketed by BASF SE under the trade description Luviskol® VA. A VP/vinyl caprolactam/DMAPA Acrylates Copolymer is marketed, for example, by Ashland Inc. under the trade name Aquaflex® SF-40. A VP/DMAPA Acrylates Copolymer is, for example, marketed by Ashland Inc. under the trade description Styleze CC-10.

in a particularly preferred embodiment of the cosmetic composition, the vinylpyrrolidone-containing polymer or copolymer comprises polyvinylpyrrolidone. In a more particularly preferred embodiment of the cosmetic composition, the vinylpyrrolidone-containing polymer or copolymer is polyvinylpyrrolidone.

Vinylpyrrolidone-containing polymers or copolymers, in particular polyvinylpyrrolidone, have been used for a long time in cosmetic compositions for the temporary shaping of hair as firming substances. Correspondingly, their chemistry, in particular their reactions with other ingredients of cosmetic compositions for the temporary shaping, of hair, is known, and this facilitates the formulation of novel products. In addition, compared with other synthetic polymers with a firming action, polyvinylpyrrolidone is an inexpensive raw material.

As the fourth essential component, the cosmetic compositions include a selected composite powder. The composite powder consists of or includes (A) powdered particles of a silicone elastomer and (B) particles of silicon dioxide. The particles of silicon dioxide (B) are immobilized on the surface of the powdered particles of the silicone elastomer (A).

Composite powders are extremely free-flowing, readily dispersible and have only a very small tendency to aggregate. They can be worked into cosmetic compositions without special equipment or specific steps of the method. As a rule, it suffices to stir the composite powder in with the other components.

Preferred composite powders are those with powdered particles having a mean particle diameter of from about 0.5 to about 100 μm, particularly preferably of from about 1 to about 10 μm.

The powdered particles of the silicone elastomer (A) may take a variety of forms in this regard, wherein spherical particles are preferred.

The powdered silicone elastomer (A) can preferably be produced by reacting an organopolysiloxane (I) which includes at least two alkenyl groups per molecule with an organopolysiloxane (II) which includes at least two hydrogen atoms per molecule bonded to a silicon atom.

In this regard, as the organopolysiloxane (I) which includes at least two alkenyl groups per molecule, a compound with formula (I):

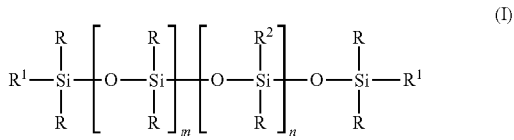

is preferably used, wherein
R represents a $C_1$-$C_6$ alkyl group or a $C_6$-$C_{10}$ aryl group,
$R^1$ represents R or an alkenyl group,
$R^2$ represents R or an alkenyl group and
m and n, respectively independently of each other, represent a whole number from 0 to about 5000,
with the proviso that in the case in which $R^1$ does not represent an alkenyl group, $R^2$ represents an alkenyl group and n is at least about 2.

Preferably, a compound with formula (II) is used as the organopolysiloxane (II) which includes at least two hydrogen atoms per molecule bonded to a silicon atom:

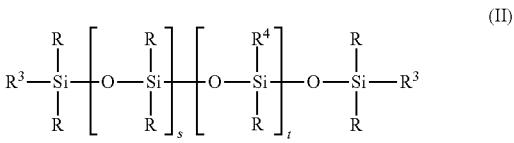

wherein
R has the meaning given above,
$R^3$ represents R or hydrogen,
$R^4$ represents R or hydrogen, and
s and t, respectively independently of each other, represent a whole number from 0 to about 5000,
with the proviso that in the case in which $R^3$ does not represent hydrogen, $R^4$ represents hydrogen and t is at least about 2.

Examples of $C_1$-$C_6$ alkyl groups which may be mentioned are methyl, ethyl, propyl and isopropyl, wherein methyl is preferred. Examples of suitable $C_6$-$C_{10}$ aryl groups are phenyl and naphthyl, wherein phenyl is preferred. Particularly preferably, R in the above formulae represents methyl.

Examples of alkenyl groups which may be mentioned are $C_2$-$C_{10}$ alkenyl, such as vinyl, allyl, propenyl, butenyl, pentenyl, hexenyl and decenyl. Preferably, the alkenyl group is vinyl.

m, n, s and t, respectively independently of each other, preferably represent a whole number from 0 to about 1000, particularly preferably from 0 to about 200.

Preferably, the powdered silicone elastomer (A) is a dimethicone-vinyldimethicone copolymer, preferably a cross-linked dimethicone-vinyldimethicone copolymer. The latter is known by the INCI name Dimethicone/Vinyl Dimethicone Crosspolymer.

The particles of silicon dioxide (B) preferably have a mean particle diameter of from about 0.001 to about 0.1 μm.

The silicon dioxide (B) is preferably amorphous and may be produced using known methods, for example by using electric arc, by using wet chemistry or by using flame hydrolysis. Preferably, the silicon dioxide (B) is fumed silica.

In order to immobilize the silicon dioxide (B) on the powdered silicone elastomer (A), the latter may, for example, be transferred into an aqueous dispersion to which the silicon dioxide (B) is added. The ratio of the quantities in this regard may be freely selected, although preferably, from about 0.1 to about 30 parts by weight of silicon dioxide (B) is added to about 100 parts by weight of powdered silicone elastomer (A). The dispersion is heated, wherein the preferred temperature range is from about 40° C. to about 95° C. Finally, the water is removed and the composite powder is obtained in this manner.

Particularly preferably, the composite powder d) is the commercially available product Dow Corning 9701 Cosmetic Powder with the INCI name Dimethicone/Vinyl Dimethicone Crosspolymer (and) Silica from Dow Corning.

The quantity of composite powder d) in the cosmetic composition is from about 0.05% to about 1% by weight and preferably from about 0.1% to about 0.8% by weight, respectively with respect to the total weight of the cosmetic composition.

The cosmetic composition includes the ingredients described above in a cosmetically acceptable support. The cosmetically acceptable support is preferably an aqueous or aqueous-alcoholic support. With respect to its total weight, the cosmetic composition preferably includes at least about 50% by weight, more preferably at least about 60% by weight and particularly preferably at least about 65% by weight of water.

Aqueous-alcoholic supports comprise water and a $C_1$-$C_4$ alcohol, in particular ethanol or isopropanol.

In addition to the aqueous or aqueous-alcoholic support, the compositions may include further organic solvents such as, for example, methoxybutanol, ethyldiglycol, 1,2-propylene glycol, n-propanol, n-butanol, n-butylene glycol, glycerin, diethylene glycol monoethylether and diethylene glycol mono-n-butylether. In this regard, any water-soluble organic solvents wherein the further organic solvent is present in a total quantity of from about 0.1% to about 15% by weight, preferably from about 1% to about 10% by weight, in particular from about 2% to about 5% by weight, respectively with respect to the total weight of the cosmetic composition, are preferred.

Preferably, the cosmetic composition includes an aqueous support and glycerin as the further organic solvent. The glycerin in particular acts to ensure that the film formed by the vinylpyrrolidone-containing polymers or copolymers on the hair does not become too solid and break even when under light mechanical loads (combing or when the user runs their fingers through their hair). Furthermore, the glycerin reduces or prevents the appearance of visually unappealing residues of product in the hair (flaking).

In particular, the cosmetic composition is in the form of a styling cream and is suitable for the temporary shaping of hair, in particular of human hair.

The cosmetic composition is preferably not free-flowing and preferably has a viscosity in the range from about 100000 to about 300000 mPas (Brookfield, TE spindle @5 rpm, about 20° C.). The container for the cosmetic compositions may be any of the types of packaging known to the person skilled in the art which are usual for cosmetic compositions for the temporary shaping of hair, such as tubes, bottles or jars.

The cosmetic composition may include further ingredients which are normal for compositions for the temporary shaping of hair.

In a preferred embodiment, the composition furthermore comprises an emulsifying agent. This may in particular serve to produce a creamy consistency.

The emulsifying agent is preferably non-ionic and may be an optionally polyoxyethoxylated fatty acid polyol ester of the fatty acid glycol monoester, fatty acid glyceryl monoester and sorbitan fatty acid ester type. Preferred examples of optionally polyoxyethoxylated fatty acid glycol monoesters are PEG-100 stearate, PEG-90 stearate, PEG-50 stearate. PEG-30 stearate, PEG-10 stearate, PEG-7 stearate. PEG-100 oleate, PEG-90 oleate, PEG-50 stearate, PEG-30 oleate, PEG-10 oleate, PEG-7 oleate, PEG-100 cocoate, PEG-90 cocoate, PEG-50 cocoate, PEG-30 cocoate, PEG-10 cocoate, PEG-7 cocoate.

Preferred examples of optionally polyoxyethoxylated fatty acid glyceryl monoesters are glyceryl stearate, PEG-30 glyceryl stearate, PEG-20 glyceryl stearate, glyceryl oleate, glyceryl cocoate, glyceryl Palmitate, PEG-18 glyceryl oleate, PEG-18 glyceryl cocoate, PEG-7 glyceryl cocoate, PEG-30 glyceryl cocoate, PEG-80 glyceryl cocoate.

Preferred examples of optionally polyoxyethoxylated sorbitan fatty acid esters are those known by the INCI names Polysorbate-20 (sorbitan monolaurate 20 EO). Polysorbate-60 (sorbitan monostearate+20 EO). Polysorbate-65 (sorbitan tristearate+20 EO), Polysorbate-80 (sorbitan monooleate+20 EO), Polysorbate-85 (sorbitan trioleate+20 EO).

Preferably, a combination of polyoxyethoxylated fatty acid glycol monoesters and fatty acid glyceryl monoesters is used as the emulsifying agent. A particularly preferred combination comprises PEG-100 stearate and glyceryl stearate.

The quantity of the emulsifying agent may be from about 0.5% to about 5% by weight and more preferably from about 1% to about 3% by weight, respectively with respect to the total quantity of the cosmetic composition.

In order to care for the hair and/or in order to endow the hair with a natural shine, the cosmetic compositions may comprise an oil.

In the context of this application, the term "oil" is used to describe a compound which is immiscible or only slightly miscible with water and which is liquid at about 25° C.

Particularly preferred oils include silicone oils which, for example, includes dialkyl and alkylarylsiloxanes such as, for example, cyclopentasiloxane, cyclohexasiloxane, dimethylpolysiloxane and methylphenylpolysiloxane, as well as hexamethyldisiloxane, octamethyltrisiloxane and decamethyltetrasiloxane.

Preferably, non-volatile silicone oils are used, which in particular include linear dimethylpolysiloxanes with kinematic viscosities (measured at about 25° C.) in the range from about 5 to about 50 cSt.

Suitable oils are selected from the esters of linear or branched, saturated or unsaturated fatty alcohols containing 2-4 carbon atoms with linear or branched, saturated or unsaturated fatty acids containing about 10 to about 16 carbon atoms, which may be hydroxylated. Isopropylmyristate and isopropylpalmitate are included in particular.

Further preferred oils are selected from symmetrical, unsymmetrical or cyclic esters of carboxylic acids with $C_{3-22}$ alkanols, $C_{3-22}$ alkane diols or $C_{3-22}$ alkane triols, for example dicaprylyl carbonate (Cetiol® CC) or glycerin carbonate.

Further preferred oils are selected from the benzoic acid esters of linear or branched C8-22 alkanols. Benzoic acid C12-C15 alkylesters, for example the commercially available product Finsolv® TN, are particularly preferred.

Oils with the INCI name Coco-Caprylate or Coco-Caprylate/Caprate are also suitable oils.

The quantity of oil may be from about 1% to about 25% by weight, more preferably from about 2% to about 20% by weight and particularly preferably from about 5% to about 15% by weight, respectively with respect to the total quantity of the cosmetic composition.

Further suitable ingredients of the cosmetic composition may include stabilizers, preservatives, fragrances or further care products.

The present disclosure also concerns the use of a cosmetic composition for the temporary shaping of hair, as well as a method for the temporary shaping of hair, in particular human hair, in which a cosmetic composition according to this disclosure is applied to the hair and it is temporarily fixed into shape.

The statements provided regarding the cosmetic compositions are also applicable mutatis mutandis to the further embodiments of the use and the methods.

The example below is intended to illustrate the subject matter of the present disclosure without in any way limiting its scope.

EXAMPLE

| Ingredient (INCI name or chemical description) | % by weight (active ingredient) |
|---|---|
| Cetearyl Alcohol | 1.5 |
| Beeswax (INCI: Beeswax) | 3 |
| PVP | 0.8 |
| Glycerin | 3 |
| Glyceryl Stearate, PEG-100 Stearate | 2 |
| Dimethicone (50 cSt) | 10 |
| Composite powder* | 0.2 |
| Sodium Polyacrylate | 0.35 |
| Preservative | 1 |
| Fragrance | 0.5 |
| Water | to 100 |

*Dow Corning 9701 Cosmetic Powder (INCI: Dimethicone/Vinyl Dimethicone Crosspolymer (and) Silica)

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A cosmetic composition for temporarily shaping hair consisting of:
   a) from about 0.5% to about 8% by weight of the total cosmetic composition is a wax with a melting point of more than about 37° C.,
   b) from about 0.5% to about 5% by weight of the total cosmetic composition is a fatty alcohol,
   c) from about 0.2% to about 2% by weight of the total cosmetic composition is a vinyipyrrolidone-containing polymer or copolymer, and
   d) from about 0.1% to about 10% by weight of the total cosmetic composition is composite powder comprising
      i) powdered particles of a silicone elastomer, and
      ii) particles of silicon dioxide,
   wherein the particles of silicon dioxide ii) are immobilized on the surface of the powdered particles of the silicone elastomer i); and
   e) at least about 50% by weight of the total cosmetic composition is an aqueous or aqueous-alcoholic support.

2. The cosmetic composition as claimed in claim 1, wherein the wax is beeswax (INCI: Beeswax).

3. The cosmetic composition as claimed in claim 1, wherein the fatty alcohol is cetearyl alcohol.

4. The cosmetic composition as claimed in claim 1, wherein the vinylpyrrolidone-containing polymer or copolymer is selected from the group consisting of polyvinylpyrrolidone, vinylpyrrolidone-vinyl acetate copolymer, Vinyl Caprolactam/VP/Dimethylaminoethyl Methacrylate Copolymer (INCI), VP/DMAPA Acrylates Copolymer (INCI) and mixtures thereof.

5. The cosmetic composition as claimed in claim 1, wherein the vinylpyrrolidone-containing polymer or copolymer is polyvinylpyrrolidone.

6. The cosmetic composition as claimed in claim 1, wherein the composite powder is a powder with the INCI name Dimethicone/Vinyl Dimethicone Crosspolymer (and) Silica.

7. A method for temporarily shaping hair in which a cosmetic composition as claimed in claim 1 is applied to the hair and the hair is temporarily fixed into shape.

8. The cosmetic composition as claimed in claim 1, wherein the wax is beeswax (INCI: Beeswax), wherein the fatty alcohol is cetearyl alcohol, wherein the vinylpyrrolidone-containing polymer or copolymer is selected from the group consisting of polyvinylpyrrolidone, vinylpyrrolidone-vinyl acetate copolymer, Vinyl Caprolactam/VP/Dimethylaminoethyl Methacrylate Copolymer (INCI), VP/DMAPA Acrylates Copolymer (INCI) and mixtures thereof;
   wherein the composite powder is a powder with the INCI name Dimethicone/Vinyl Dimethicone Crosspolymer (and) Silica.

* * * * *